United States Patent
Fisher et al.

(10) Patent No.: US 8,455,000 B2
(45) Date of Patent: Jun. 4, 2013

(54) RESORBABLE POLYMER COMPOSITIONS FOR USE IN MEDICINE, DENTISTRY, AND SURGERY

(75) Inventors: Timothy C. Fisher, Los Angeles, CA (US); Jonathan K. Armstrong, Los Angeles, CA (US); John Cambridge, Los Angeles, CA (US); Tadeusz Z. Wellisz, Los Angeles, CA (US)

(73) Assignee: Syncera Inc., Los Angeles, CA (US)

( * ) Notice: Subject to any disclaimer, the term of this patent is extended or adjusted under 35 U.S.C. 154(b) by 652 days.

(21) Appl. No.: 12/302,288

(22) PCT Filed: May 22, 2007

(86) PCT No.: PCT/US2007/012122
§ 371 (c)(1), (2), (4) Date: Nov. 24, 2008

(87) PCT Pub. No.: WO2007/139760
PCT Pub. Date: Dec. 6, 2007

(65) Prior Publication Data
US 2009/0286886 A1    Nov. 19, 2009

Related U.S. Application Data

(60) Provisional application No. 60/802,115, filed on May 22, 2006.

(51) Int. Cl.
*A61K 9/14* (2006.01)

(52) U.S. Cl.
USPC .......................................................... 424/486

(58) Field of Classification Search
USPC .......................................................... 424/486
See application file for complete search history.

(56) References Cited

U.S. PATENT DOCUMENTS

| 4,013,622 | A | 3/1977 | Dejuneas et al. |
| 6,770,688 | B1 | 8/2004 | Miyamoto |
| 7,135,508 | B2 * | 11/2006 | Chaiko et al. ............ 523/216 |
| 7,553,913 | B2 | 6/2009 | Wellisz et al. |
| 2003/0095945 | A1 | 5/2003 | Levy et al. |
| 2006/0100370 | A1 | 5/2006 | Wellisz et al. |
| 2006/0140904 | A1 | 6/2006 | Wellisz et al. |
| 2006/0141040 | A1 * | 6/2006 | Chen et al. ............ 424/486 |

FOREIGN PATENT DOCUMENTS

| FR | 2859988 | 3/2005 |
| JP | 07179804 | 12/1993 |

OTHER PUBLICATIONS

Int'l Search Report for PCT/US2007/012122, one page, dated Aug. 21, 2008.
Written Opinion for PCT/US2007/012122, three pages, dated Aug. 21, 2008.
Wellisz et al. "Ostene, a new water-soluble bone hemostasis agent" J. Craniofac. Surg. 17:420-425 (May 2006).
Wellisz et al. "The effects of a soluble polymer and bone wax on sternal healing in an animal model" Ann. Thorac. Surg. 85:1776-1780 (May 2008).
Int'l Preliminary Report on Patentability for PCT/US2007/012122, mailed Dec. 11, 2008.

\* cited by examiner

*Primary Examiner* — Paul Dickinson
(74) *Attorney, Agent, or Firm* — Nixon & Vanderhye PC (57) ABSTRACT

We describe the medical, dental, and surgical uses of modified poly(alkylene) materials which are fully resorbable after implantation into the body, and compositions formulated with such modified poly(alkylene) materials.

30 Claims, 2 Drawing Sheets

100% PE-PEG

Figure 1A

90% PE-PEG/10% Poloxamer 124

Figure 1B

80% PE-PEG/20% Poloxamer 124

Figure 1C

50% PE-PEG/50% Poloxamer 124

Figure 1D

30% PE-PEG/70% Poloxamer 124

Figure 1E

10% PE-PEG/90% Poloxamer 124

Figure 1F

100% Poloxamer 124
The curved line is part of a small
air bubble in the liquid polymer.

RESORBABLE POLYMER COMPOSITIONS FOR USE IN MEDICINE, DENTISTRY, AND SURGERY

CROSS-REFERENCE TO RELATED APPLICATIONS

This is a U.S. national-stage application under 35 U.S.C. 371 of Int'l Appln. No. PCTUS2007/012122, filed May 22, 2007; which designated the U.S. and claims priority benefit of provisional U.S. Application No. 60/802,115, filed May 22, 2006; the entire contents of which are hereby incorporated by reference herein.

FIELD OF THE INVENTION

This invention relates to the use in medicine, dentistry, and surgery of modified poly(alkylene) materials which are resorbable after implantation into the body, and to compositions formulated with such modified poly(alkylene) materials.

BACKGROUND OF THE INVENTION

Nontoxic, biocompatible, resorbable materials that are flowable or malleable, and have grease-like or wax-like properties are highly desirable for a wide range of medical and surgical applications. Such applications include use as a lubricant to facilitate the insertion or positioning of devices such as catheters or other implantable devices, use as an adhesive putty to keep devices and materials in position during a procedure, use as a barrier to prevent the movement of fluids away from or into tissues, or to prevent adjacent tissue surfaces from sticking together, and use as an adhesive and cohesive carrier or matrix for bioactive or inert particles and drugs that can be applied directly to bone or other tissues during surgery to promote healing.

Resorbable materials used in medicine, dentistry, and surgery are often based on hydrogels, consisting of a network of hydrophilic polymers in an aqueous medium. Hydrogels are generally well suited for use in contact with body tissues, having good biocompatibility, low toxicity, and solubility or resorbability, but the physical and mechanical properties of hydrogels are dissimilar to those of hydrocarbon-based materials and are generally less than ideal for applications that require any manipulation during their use. Chemically crosslinked hydrogels may be somewhat elastic but are not malleable or flowable because their gel structure cannot be remodeled. Once the gel structure is broken, the chemical bonds that link the polymer molecules into a network cannot be restored, and thus exposure to a force beyond the elastic limit results in fracture rather than plastic deformation. Once fully cured, such hydrogels cannot be molded or manipulated, and can be difficult to keep in place.

In some other types of hydrogel, the polymer molecules are not joined by covalent bonds, but by hydrophobic or electrostatic interactions, which can be dispersed by a change in temperature, pH, or ion concentrations, or by physical manipulation. Since the bonding is reversible, such gels may exhibit true malleable or flowable properties but, because the bonding forces are relatively weak, materials of this type are usually very soft gels with a low elastic modulus and minimal resiliency.

The high water content of hydrogels is not always desirable. Hydrogels that are not fully saturated with water prior to use, or which become more osmotically active during the resorption process, will take up additional water and consequently increase in volume after implantation. It the swelling of the implanted material occurs in an enclosed space within the body there can be a significant rise in pressure with resultant tissue damage. Also, if these compounds are intended to serve as a carrier for particles, drugs or other materials to enhance local healing, the swelling is likely to cause displacement of the particles away from the intended site. A further disadvantage of such materials is that many drugs and most bioactive compounds have reduced stability in the presence of water, thus a hydrogel-based carrier for such agents would need to be supplied in dry form and not as a ready-to-use material.

Oils and waxes from petroleum, or of plant or animal origin, often have ideal mechanical and physical properties for use as putty-like adhesives, cohesive matrices, lubricants of all weights, and barriers. Examples include mineral hydrocarbons such as petroleum jelly and paraffin wax, natural hard waxes such as beeswax and carnauba wax which are esters of long chain alkanes, and many types of synthetic or modified waxes. Depending upon the average molecular weight, extent of branching and degree of unsaturation of the hydrocarbon components of these materials, their physical properties can range from liquid, through soft flowable gel, gum, malleable soft wax, brittle hard wax, to soft plastics (e.g., polyethylene). Unfortunately, these substances are hydrophobic, insoluble in water or other aqueous media, and chemically inert. As a consequence, they cannot be dissolved, resorbed, metabolized or otherwise removed by the body, and once introduced into the tissues, will remain at the site of application indefinitely. Over time, the wax or grease will cause inflammation and interfere with healing.

Although the inability of the body to resorb such materials is known, it nevertheless remains common surgical practice to use a beeswax formulation to stop bleeding from the surface of cut bone. Bone is a structure with a rich blood supply that circulates through a system of canals within the hard mineralized matrix, and extensive network of vessels within the bone marrow. Bleeding from out or damaged bone cannot be stopped by the same techniques used for soft tissues, such as by applying hemostatic clamps or electrocautery. A beeswax formulation applied to the cut surface arrests the bleeding very effectively by adhering to the bone and physically occluding the open blood vessels. The disadvantage of beeswax is that it is not resorbed, and remains at the application site long after the surgery, where causes inflammation and sometimes granuloma formation, and interferes with bone healing. As a foreign body, the residual wax may also become a focus for persistent bacterial infection. Several resorbable formulations have been developed as alternatives to beeswax-based bone wax, and for many other surgical applications, including lubricants, barriers, and matrices, but all such material in the prior art have proven to be suboptimal in terms of biocompatibility, physical properties and handling characteristics, appearance, having ingredients of biological origin, complexity of formulation, ease of manufacture, and/or stability.

Therefore, it is an object of this invention to provide an alternative to wax- and grease-based materials for use in medical, dental, and surgical applications that overcomes the known deficiencies of existing materials.

Porous implant materials are useful for the repair or reconstruction of the bony skeleton. Implants can be used to fill bony defects, or they can be to augment or replace bone or cartilage in humans or in animals. Such implants may be made by sintering small particles or beads of a fusible material such as polyethylene or metal. An alternative way to make a porous material is to blend air bubbles or leachable particles into a molten substrate, such as titanium, which is then cooled. The particles are removed by chemical means after the substrate has cooled, leaving a "negative" structure, wherein the metal fills the spaces that existed between the particles. Typically the objective is a highly porous material in which the pores form an interconnecting network. Tissue ingrowth occurs in implants with interconnecting pores of 60 microns or greater average diameter. Collagen is deposited within the pores to form a highly stable infection-resistant complex that does not behave as a foreign body, and becomes effectively integrated with the tissues into which it was placed. For a porous compound to be effective as an implant material, it must be biocompatible, mechanically stable, and have stable, interconnecting pores that are large enough to allow tissue ingrowth. The material must be nontoxic and nonimmunogenic, have a stable shelf life, and importantly, it must have good handling characteristics and be sufficiently easy to use in a clinical setting. Present porous implant materials have two significant disadvantages; due to their highly porous structure: the surface of such materials is rough and abrasive, and has a high coefficient of friction when in contact with tissues. This is especially true for porous metal implants with a negative or foam-like structure which may be extremely abrasive, especially if they have large pore sizes. It can therefore be difficult to move porous implants into position during surgery, and the implant surface tends to collect debris such as fat and cellular material which can later become necrotic and harbor infection. There is a need to reduce the surface roughness without compromising the porosity of the material, and to prevent accumulation of debris. This can be achieved by filling or covering the pores with a resorbable or soluble substance.

Therefore, it is another object of this invention to provide a porous implant in which the pores are filled or covered with a resorbable substance that is water soluble and becomes lubricious when wet, resulting in an implant with a smooth surface, without cavities in which debris can become trapped, and with a lubricating layer which helps the surgeon to slide the implant through tissue planes during placement.

In the fields of medicine, surgery, and dentistry, there is a need for an implantable material that contains a particulate component to serve as a framework for tissue ingrowth. The particulate component can be selected from a broad range of natural and synthetic implantable substances, including, but not limited to, native autogenous bone or cartilage, bone or cartilage from other sources that is either grafted directly or after processing, collagen, hydroxyapatite, polymethylmethacrylate (PMMA), polytetrafluoroethylene (PTFE), polyethyllone, and dimethylpolysiloxane. The performance of particulate implants are markedly improved by the addition of a matrix to temporarily adhere the particles to one another, and to form a putty that serves to improve the handling characteristics and to act as a delivery system. The majority of matrices disclosed in the prior art are hydrogels, and they include collagen, glycerol, polysaccharides, mucopolysaccharides, hyaluronic acid, and plasdones (e.g., polyvinylpyrrolidone, PVP). They are not essential for this invention.

Collagen, in the form of gelatin) has been used in ARTEPLAST® from Rofil Medical International. It is an injectable material comprised of microspheres of poly-methylmethacrylate (PMMA) suspended in a gelatin solution. Following implantation, the gelatin is resorbed and replaced by native collagen. Another formulation, ARTE-COLL® is a product currently available in Europe and Canada. It is comprised of smooth PMMA spheres, suspended in bovine collagen from a closed pharmaceutical herd at a concentration of 25% PMMA/75% collagen, by weight with 0.3% lidocaine. Because ARTECOLL® contains bovine collagen, skin testing for allergy to bovine collagen is recommended. Bovine collagen carries the risk of an immunogenic reaction by the recipient patient. Recently, it has been found that a disease of cattle, bovine spongiform encephalopathy (BSE) is transmitted from bovine tissue to humans. Thus, bovine collagen carries a risk of disease transmission and is not a desirable matrix for allograft bone. Human collagen is free of these animal-based diseases. But, collagen absorbs slowly in the human body, particularly in a bony site with a low degree of vascularity.

Glycerol is used as a matrix for demineralized allograft bone in the form of a gel. For example, GRAFTON® from Osteotech is a simple mixture of glycerol and lyophilized, demineralized bone powder (U.S. Pat. No. 5,073,373). GRAFTON® works well to allow the surgeon to place the allograft bone at the site. But glycerol has a very low molecular weight (92 daltons) and is very soluble in water, the primary component of the blood which flows at the surgical site. Glycerol also experiences a marked reduction in viscosity when its temperature rises from room temperature (typically 22° C. in an operating room) to the patient's body temperature (typically 37° C.). This combination of high water solubility and reduced viscosity causes the allograft bone with a glycerol matrix to be runny and to flow away from the site almost immediately after placement. This prevents the proper retention of the allograft bone within the site as carefully placed by the surgeon. The use of the low-molecular weight glycerol carrier also requires a high concentration of glycerol to be used to achieve the bulk viscosity. Glycerol and other low-molecular weight organic solvents are also toxic and irritating to the surrounding tissues.

U.S. Pat. No. 4,191,747 discloses a bone defect treatment with denatured bone meal freed from fat and ground into powder. The bone meal is mixed with a polysaccharide in a solution of saline and applied to the bone defect site. U.S. Pat. No. 5,290,558 discloses a flowable, demineralized bone powder composition using an osteogenic bone powder mixed with a low molecular weight polyhydroxy compound from 2 carbons to about 18 carbons in chain length including a number of classes of different sugars such as monosaccharides, disaccharides, water-dispersible oligosaccharides, and polysacaharides. U.S. Pat. No. 5,356,629 discloses making a rigid gel in the form of a bone cement to fill defects in bone by mixing biocompatible particles preferably PMMA coated with polyhydroxyethylmethacrylate in a matrix (e.g., hyaluronic acid) to obtain a molded semisolid mass which can be suitably worked for implantation into bone. The hyaluronic acid can also be utilized in monomeric form or in polymeric form preferably having a molecular weight not greater than about one million daltons. It is noted that the nonbioabsorbable but biocompatible particles can be derived from xenograft bone, homologous bone, autogenous bone, as well as other substances. The bioactive substance can also be an osteogenic agent such as demineralized bone powder, in addition to morselized cancellous bone, aspirated bone marrow, and other autogenous bone sources. This is a cement used for implantation of hip prosthesis.

U.S. Pat. No. 6,281,195 discloses a poloxamer hydrogel matrix for the delivery of osteogenic proteins. In particular, poloxamer 407 (PLURONIC™ F127) is used in the form of a hydrogel. Int'l Patent Application PCT/US2004/004174 teaches the use of alloys of alkylene oxide block copolymers and random alkylene oxide copolymers for medical applications, and these formulations also do not rely on water for their utility. But, the alkylene oxide copolymer alloys and the random alkylene oxide copolymers have overall hydrophilic properties, and thus may share some of the limitations of hydrogels with regard to their swelling tendency after implantation.

Therefore, it is yet another object of this invention to provide a nonhydrogel polymer matrix for certain particulate materials used in medicine, dentistry, and surgery which provides a superior combination of adhesive and cohesive properties, ease of handling, optimal retention time at the site of application, minimal swelling, and which is made from non-biological compounds and is manufactured and used in an essentially anhydrous state.

The present invention teaches that long chain poly(alkylene) molecules suitably modified with poly(ethylene glycol) (PEG) have the properties of greases or waxes but are soluble or dispersible in water; a combination of properties that makes ideally suited for numerous medical, dental and surgical uses. The use of these compounds and novel formulations of these compounds with other materials disclosed herein for such applications have not previously been.

SUMMARY OF THE INVENTION

We describe a biocompatible, generally nonmetabolizable, water-soluble or dispersible composition based upon poly(alkylene)-poly(ethylene glycol) block copolymers, with at least 40 carbon atoms in the poly(alkylene) block, for use in parenteral and topical applications in medicine, dentistry, and surgery. These poly(alkylene)-poly(ethylene glycol) block copolymers may be used alone or may advantageously be further combined, mixed, or blended with one or more other polymers, or with inert fillers, bioactive compounds, or particles.

The poly(alkylene)-poly(ethylene glycol) block copolymers (termed PA-PEGs herein) and formulations thereof have ideal properties for use as a surgical adhesive, hemostatic agent, surgical lubricant, excipient for implantation, or as a cohesive matrix to hold small objects in place at a site of surgery, such as bone fragments or particulate materials. For such applications, the PA-PEG material advantageously overcomes the lack of resorbability that has hitherto been a barrier to the use of grease-like or wax-like polyalkylenes in medicine, dentistry, and surgery. For example, the PA-PEG material can achieve the hemostatic effects of beeswax blends, but will be eliminated from the site of application within days to weeks, and therefore will not compromise wound healing or persist as a foreign body. The nature of the PA-PEG material is such that it is likely to be cleared almost entirely by excretion and is unlikely to be substantially metabolized in the body.

The rate of resorption may be controlled by varying the molar ratio of the poly(alkylene) and poly(ethylene glycol) components, which allows the design of PA-PEG material that remains at the site of implantation for a prolonged duration, but will eventually be resorbed when no longer needed. PA-PEG material with a high ratio of poly(alkylene) to poly(ethylene glycol) are hydrophobic on balance and thus will dissolve slowly in an aqueous environment, and can be advantageously used to retain inert or bioactive substances or particles at the application site for an extended period of time.

Moreover, the poly(alkylene) component of the PA-PEG material has little tendency to absorb water. Thus, in contrast to many other resorbable materials used in medicine, dentistry, and surgery, the risk of injury such as nerve damage or occlusion of blood vessels due to pressure from the swelling of the implanted material is minimized. The lack of swelling is also particularly desirable when the material is used as a matrix to position and retain particles at the site of treatment, because any post-operative expansion of the matrix may result in displacement of the particles from their intended position.

Furthermore, the material's properties can be readily varied by blending two or more different types of PA-PEG material together or by blending a PA-PEG with a compatible or miscible polymer (e.g., a low molecular weight PEG or a polyethylene glycol-polypropylene glycol copolymer, such as a poloxamer), without the need to include any water in the formulation.

DESCRIPTION OF SPECIFIC EMBODIMENTS OF THE INVENTION

The invention relates to the medical, dental, and surgical applications of poly(alkylene) molecules modified by the addition of one or more poly(ethylene glycol) (PEG) chains to form block copolymers of the general formula:

where n represents the average number of carbon atoms in the poly(alkylene) chain, x represents the average number of repeating ethylene oxide monomer units that comprise each poly(ethylene glycol) chain, and y represents the number of poly(ethylene glycol) chains attached to each poly(alkylene) molecule. In the simplest case, where each poly(alkylene) molecule carries a single PEG chain, y=1 and therefore the formula reduces to:

In common usage, alkanes and their alcohol or acid derivatives are often referred to by a "C value" which indicates the number of carbon atoms occurring along the alkane chain (e.g., C16 for palmitic acid or C18 for stearic acid). Thus, in the current notation, n and Cn are equivalent.

All PA-PEG molecules in which the PA component is a single linear alkane molecule of the formula $CH_3$—$(CH_2)_n$—L, where L denotes the linkage to the PEG chain, will be termed poly(ethylene)-PEG or PE-PEG for the purposes of this application. This terminology is adopted for simplicity, but is not intended to exclude molecules in which n is an odd number, nor molecules that are named using the common name of the equivalent long chain alcohol or fatty acid, such as tricontanol-PEG (i.e., $C_1H_3$—$(CH_2)_{29}$—O-PEG) or palmitic acid PEG ester (i.e., $CH_3$—$(CH_2)_{14}$—CO—O-PEG). Nor does it exclude the possibility of unsaturated carbon-carbon bonds in the poly(alkylene), long chain alcohol, or fatty acid component. PE-PEG molecules with branching in the PE component are also not necessarily excluded and are referred to as branched-PE-PEG. PA-PEG molecules can be conveniently further specified by the average number of carbon atoms in the PA component, and the average degree of polymerization of the PEG component: i.e., the number of moles of ethylene oxide residues per mole of PA. Thus, a PE-PEG with n=50 (i.e., 50 carbon atoms in the PE chain) and a PEG component polymerized from an average of eight EO molecules, is referred to as C50 PE-PEG8.

The poly(alkylene) component of the PA-PEG may be a linear or branched alkane or poly(ethylene), or a polymer of propylene, trimethylene, butylene, isobutylene or another low molecular weight alkylene monomer, or copolymers thereof. If side groups or branches are formed along the length of the PA polymer backbone, then the PA-PEG will typically be softer and less crystalline than a poly(ethylene)-PEG due to differences in the interactions between adjacent poly(alkylene) molecules and the resulting differences in the packing and crystal structure of the material in the solid form. A specific example of a branched alkane polymer suitable for use is a Guerbet alcohol, which has a branch at the 2 position of the alkane, such as 2-hexadecyl octadecanol, a C34 alcohol. Guerbet alcohols have low melting points for their molecular weight, making them good lubricants with much lower irritation and toxicity potential than a linear saturated aliphatic alcohol with a similar melting point, and superior resistance to oxidation compared to unsaturated oils.

The desired physicochemical properties of a PE-PEG can be selected by choosing appropriate values of n, x, and y. At temperatures between ambient and body temperature (e.g., about 20° C. to 37° C.), PE-PEG molecules with higher values of n are typically waxy solids, while those with lower n resemble greases or soft waxes. The hardness and crystallinity of PE-PEGs also increases with the length of the PEG chain (x) and the number of PEG chains present (y). With short PEG chains (i.e., low x), the mechanical properties of PE-PEG are similar to those of an unmodified poly(ethylene) of equivalent n. With large PEG chains (high x), especially if several chains are attached to the same molecule, PE-PEGs become harder and more brittle. Since the PE component is strongly hydrophobic but the PEG component is hydrophilic, adjusting the ratio between n and (x times y) varies the overall hydrophobicity of the PE-PEG molecule. It will be apparent to a person with knowledge of such polymers that as x, or (x times y) for molecules with multiple PEG chains, becomes very much larger than n, the properties of PA-PEGs will approach those of an unmodified PEG molecule. Thus, there is an upper limit on the ratio of x to n, or (x times y) to n, above which a PE-PEG molecule would not exhibit the desired greasy or waxy properties.

It is known that molecules having linear alkane chains with n values of 20 or lower (e.g., C12-C20 alcohol PEG ethers, commercially available as "Brij" surfactants) have strong detergent properties and can disrupt the membrane of biological cells leading to hemolysis of red blood cells and in vitro cytotoxicity for other cell types. The hemolysis and toxicity are believed to occur because alkane chains with $n<=20$, have a similar length to the lipid tails of the phospholipids molecules that make up cell membranes, and are thus able to insert into the membrane, causing disruption and possibly emulsification due to their strong surfactant properties. Similar molecules with longer alkane chains (e.g., greater than 40 carbon atoms) do not appear to cause hemolysis and are expected to have reduced or negligible cytotoxicity. Thus, PA-PEGs with $n>40$ are expected to be of greatest value for most of the medical, dental, and surgical applications disclosed in this application.

Some C33 and C50 PE-PEG compounds are commercially available Sigma-Aldrich (St. Louis, Mo.) supplies five different poly(ethylene)-PEGs (PEPEGs), each with a single PEG chain, as shown in Table 1.

TABLE 1

| Catalog # | Mn | wt. % PEG | n | x | y | Name |
|---|---|---|---|---|---|---|
| 459003 | ~575 | 20 | 33 | 2.5 | 1 | C33 PE-PEG2 |
| 458988 | ~920 | 50 | 33 | 10 | 1 | C33 PE-PEG10 |
| 525901 | ~2250 | 80 | 33 | 41 | 1 | C33 PE-PEG40 |
| 458996 | ~875 | 20 | 50 | 4 | 1 | C50 PE-PEG4 |
| 458961 | ~1400 | 50 | 50 | 16 | 1 | C50 PE-PEG16 |

PA-PEGs having the desired combinations of n, x and y can be synthesized by known polymer chemistry techniques.

One general method to produce a PE-PEG is described as follows:

1) A borane-terminated polyethylene (PE) chain is first prepared by metaliocene-mediated olefin polymerization of ethene (ethylene) in the presence of 9-borabicyclo[3.3.1]nonane (9-BBN) as a chain transfer agent. This has the benefit of ensuring the PE chain grows to the correct size and leaves an easily activated end group available for further reaction.
2) The terminal borane group is then oxidized with sodium hydroxide and hydrogen peroxide to produce a hydroxyl-terminated PE chain (PE-t-OH).
3) The PE-t-OH is converted to the metallated derivative (PE-t-OK) with potassium napthalide.
4) A poly(ethylene glycol) chain is added by anionic ring opening polymerization of ethylene oxide.

With this technique, the degree of polymerization of the PE chain (and hence the molecular mass and n value for each chain) can be controlled by varying the proportion of 9-BBN relative to the metallocene initiator. For the PEG chains, the degree of polymerization of the PEG (i.e., x) is controlled by adjusting the proportion of ethylene oxide (EO) added to the reaction relative to the amount of the PE-t-OK. The EO polymerization essentially starts at the same time on every PE-OK molecule and propagates at the same rate on each of them until all EO monomers have reacted. Thus an approximately equal amount of EO is added to each PE chain.

An alternative method to make the same type of PE-PEG is to obtain a commercially-available long chain primary alcohol as a starting material. Such alcohols are available in the range up to C60, for example, the UNILIN alcohols from Baker Petrolite with average chain lengths of C24 to C50. The long chain alcohol may then be modified as described in steps 3 and 4, eliminating steps 1 and 2.

A long chain carboxylic acid may also be advantageously used as a starting material for PE-PEGs. For example, PE-PEG molecules may be modified by grafting a PEG molecule to each carboxylic acid molecule, thus avoiding the need to use highly toxic ethylene oxide gas during synthesis. Typical grafting techniques create an ester bond between the carboxylic acid group and one terminal hydroxyl group on the PEG molecule. A further possibility is to create an amide bond using a PEG derivative with a terminal amino group. Other types of bond between the poly(alkylene) and the PEG components are also possible. However, the physical properties of the long-chain PA-PEG molecules will be predominantly dependent upon the absolute and relative molecular masses of the PA and PEG components, regardless of the specific type of chemical bond that links the components together.

It is considered likely that each of the medical, dental, and surgical applications and preferred embodiments presented herein could be met using a single customized PA-PEG compound without any need to combine the PA-PEG with another chemical or polymer. The properties of the PA-PEG would be specifically designed for the application by choosing a suitable molecular weight and degree of branching for the PA block, and adding one or multiple PEG blocks each with an appropriate number of EO units.

Although such use of a pure PA-PEG alone has advantages, small scale synthesis of such compounds is likely to be relatively expensive. A practical and cost effective alternative is to take an existing PA-PEG compound that is produced in quantity, ideally a commercially available compound, and adjust its properties to meet the requirements of the intended application by blending with another suitable material.

Traditional hemostatic bone waxes are formulated with beeswax, a relatively hard wax comprised principally of the long-chain aliphatic esters tricontanylpalmitate (C46) and melissylpalmitate (C48). To create a hand-moldable waxy formulation with the desired handling properties for use as a hemostatic agent, the beeswax is blended with an appropriate amount (e.g., about 15% to about 30%) of an alkane or alkane ester of lower molecular weight, such as almond oil, petrolatum, ethyl palmitate or isopropyl palmitate, which serves to soften the blend.

The same principle can be applied to PA-PEG compounds. PA-PEGs of higher molecular weights are expected to be more biocompatible and to have lower toxicity, but will also tend to be harder and to have higher melting points. Thus, in general, but not necessarily in all cases, a primary objective of blending the PA-PEG with a second material will be to produce a blend that is softer, more malleable and possible more adhesive and cohesive between 20° C. and 37° C. than the unblended PA-PEG compound while retaining the advantages of lower toxicity associated with the higher molecular weight. A suitable material for blending would be expected to be a soft paste or liquid between 20° C. and 37° C.

For the applications anticipated herein, the material to be blended with the PA-PEG must also be chemically stable, nonvolatile, nontoxic, biocompatible, and resorbable, and preferably also water-soluble or dispersible after implantation into the body. A survey was therefore conducted to search for biocompatible polymers that could be successfully blended with commercially available PE-PEG compounds. Those polymers which showed compatibility in preliminary evaluations were evaluated in more detail to establish the range of proportions of PE-PEG to polymer that produced a stable blend, and to establish the extent of compatibility of the two materials based their macroscopic appearance and the physical characteristics of the blend when molten and when solid.

It is known in the art that polymers of different types are usually incompatible and if mixed together, will usually spontaneously separate into individual phases. Compatibility of a two-polymer melt is unusual, and even if no gross separation is seen on standing or cooling, the presence of individual phases can often be clearly seen under the microscope. Thus, an unexpected result of these studies was that a number of polymers were identified that appeared to form miscible blends with PE-PEG. To further evaluate these polymers, the blends were examined by polarized light microscopy for evidence of phase separation on the microscopic scale. A summary of these experiments is presented in Examples 1 and 2.

Of particular note, two poloxamers, P124 and P235 formed stable and apparently miscible blends with C50 PE-PEG16, with no evidence of phase separation in either the molten or solid state over a wide range of proportions, even under the microscope. Thus we can say that these compounds are miscible, at least down to the micron or sub-micron scale. The miscibility of the polymers causes the blend to behave as a true alloy with physical properties that reflect the relative proportions of the two component polymers, and exhibit advantageous properties that are not exhibited by either component polymer alone.

The discovery of novel, apparently miscible, blends of PE-PEG with poloxamers, a class of water-soluble and generally nontoxic polymers, is an unexpected and very desirable finding. The ability to blend PE-PEG with another water-soluble polymer allows the handling properties of the formulation to be adjusted from a soft waxy paste to a medium-hard solid, resembling candle wax, by varying the relative proportions of PE-PEG and the second polymer. In this manner, resorbable formulations suitable for a wide range of applications can be made that: i) are not gels or hydrogels, ii) do not contain a significant amount of water, and iii) are used without the addition of water or other aqueous media.

In a preferred embodiment, a solid poly(ethylene)-block-poly(ethylene glycol) having about 50 alkane carbon atoms, similar to the major component of beeswax (e.g., C50 PE-PEG16), is blended with a compatible or miscible second polymer, such as poloxamer 124, poloxamer 234 or poloxamer 235 (PLURONIC™ L44, P84 and P85, BASF). The combination produces a malleable, hand-moldable, adhesive, cohesive, wax-like material that closely resembles beeswax-based hemostatic bonewax in form, feel, and function, and is effective for bone hemostasis during medical, dental, or surgical procedures. A major advantage of this PE-PEG formulation is that it is entirely comprised of water-soluble or water-dispersible polymers, and will slowly wash away from the site of application, in contrast to the hydrophobic and insoluble materials contained in beeswax-based bonewax.

A blend of two or more different PA-PEGs, such as a blend containing a linear PE-PEG and a branched PE-PEG, especially a Guerbet-type PE-PEG, is considered to be particularly advantageous, because the nature of the blended material in the solid state can be varied over a wide range, from oily liquid to hard waxy solid, by varying the relative proportions of the components. Such PA-PEG blends also have the additional advantage that all components are chemically almost identical, with only minor differences in the molecular weight or branching of the PA or PE blocks. In a preferred embodiment, a PE-PEG that is a solid below 37° C., such as C50 PE-PEG 16 is blended with PE-PEG or PA-PEG that is a soft paste or liquid at about 37° C. or below, such as a C40 to C60 branched-PE-PEG16, prepared from a Guerbet-type 2-branched alkyl alcohol or acid, in appropriate proportions to produce a semi-solid to solid as material with the desired softness and malleability.

In another preferred embodiment, a soft and malleable PA-PEG, PA-PEG blend, or a PA-PEG blended with another water-soluble or water-dispersible polymer (PA-PEG/polymer blend), is combined with up to 65% by volume of a solid inert particles, such as hydroxyapatite or polyethylene particles, to provide an implantable putty-like filler material to support tissue or bone growth into a bony defect. The optimal particle size (i.e., the largest dimension) is in the range from about 35 microns to about 500 microns (preferably about 50 microns to about 300 microns); below 35 microns the particles are susceptible to removal or migration by phagocytosis, while particles greater than 500 microns in diameter do not form a material with a putty or paste-like consistency. The PA-PEG, PA-PEG blend, or PA-PEG/polymer blend serves as a cohesive and adhesive matrix which allows the particles to be positioned into a defect in bone or other hard tissue during a surgical procedure. After the surgery, the matrix slowly disperses at a controlled and predictable rate with minimal adverse reaction by the tissue, leaving a framework of solid particles interspersed with pores into which connective tissue or bone can grow.

As an example, polyethylene particles ranging in size from about 50 microns to about 300 microns are combined in a matrix consisting of C50 PE-PEG16 (65% w/w) blended with poloxamer 124 (35% w/w) with no added water. The resultant malleable putty can be used to fill defects in bone, such as cranial defects. The matrix performs two important tasks: it provides the cohesion required to keep the particles together and serves to adhere to the tissues during application. The minimal swelling and relatively slow dissolution rate of the PE-PEG blend serves to retain the particles at the site, allowing time for tissue ingrowth into the inter-particle spaces. In this regard, the PA-PEG based matrix is superior to the prior art.

In addition to inert particles, a malleable PA-PEG, PA-PEG blend, or PA-PEG/polymer blend can be used as a cohesive matrix for pieces or particles of bone, either as an adhesive substrate to assist with the positioning of multiple bone fragments or as a cohesive matrix for ground particles of autologous or allogeneic (allograft) bone. Allograft bone can also be demineralized to leave the underlying collagen structure containing active bone morphogenic proteins, known as demineralized bone matrix (DBM). DBM is naturally both osteoinductive and osteoconductive, and is used in bone surgery to fill osseous defects, becoming fully incorporated in the patient's tissue, DBM is available lyophilized to provide for extended shelf life, but in this form it is usually coarse, dry, and difficult to manipulate by the surgeon. The patients own blood may be used as a vehicle in which to mix the dry DBM to form a defect-filling paste. As a more convenient alternative, DBM is supplied as a paste or putty mixed with a variety of different liquid materials including glycerol, hyaluronic acid, gelatin, and poloxamer 407. Glycerol is a low molecular weight liquid which rapidly flows out of the DBM, is poorly cohesive, and does not promote adhesion to the site of application. At high concentration, glycerol is also hypertonic and potentially cytotoxic when applied to tissues, but does have the advantage that the DBM is not exposed to water as part of the formulation, which may protect the activity of the DBM during storage. Hyaluronic acid, glycerin, and poloxamer-based matrixes are aqueous solutions of hydrophilic polymers (i.e., hydrogels) which tend to swell and rapidly disperse after implantation, and which necessarily expose the DBM to water which may compromise the activity of the osteogenic substances that it contains.

Thus, in a preferred embodiment, an appropriately soft and malleable, and essentially anhydrous PA-PEG, PA-PEG blend, or PA-PEG/polymer blend is combined with lyophilized DBM by mixing in a cool, dry environment in appropriate proportions to produce a paste or putty with properties for use as an osteoinductive/osteoconductive defect-filling implantable material. The PA-PEG, PA-PEG blend, or PA-PEG/polymer blend matrix has superior cohesive and adhesive properties than existing carriers for DBM and does not expose the DBM to water at any time during manufacture or storage, and has a lower swelling tendency, and disperses more slowly, than more hydrophilic polymers such as hyaluronic acid and poloxamer 407.

Placement of porous implants made from polyethylene, hydroxyapatite, titanium, and other polymers and metals into bone defects is a common surgical procedure. Implant materials that allow for bone to grow into the pores are considered to be osteoconductive. Implants that have a bioactive component that induce bone formation, such as implants made from a bone removed from a different location, are considered to be osteoinductive. In the event that it is desirable that native bone eventually replaces the implant, a material that can be remodeled by the body may be preferable. In certain other clinical situations, such as a defect in the adult human cranium, the bone is not expected to grow, and a nonresorbable porous implant material such as sintered polyethyllene is preferred. The majority of porous implants that allow for tissue ingrowth are grossly solid structures with a microporous structure. To be clinically useful, they often need to be sculpted by the surgeon into their desired form. The microporous structure is exposed at the surface of the implant, making the surface rough and abrasive, which can cause the implant to adhere to or scrape against tissue during attempts to insert it into the desired position, much like a piece of VELCRO® fabric. Deposition of cellular and other debris and infectious bacteria into the open pores is another undesirable drawback to the use of porous implants. To decrease the risk of bacterial infection, the implant may be soaked in an antibiotic solution prior to use.

In another preferred embodiment, a suitable PA-PEG, PA-PEG blend, or PA-PEG/polymer blend is applied to a porous implant material, either as a surface coating or as a space-filling matrix, to provide the implant with pores that are temporarily filled with a solid but water-soluble and highly lubricious material. The coating or matrix makes the implant surface smoother and less abrasive, which reduces the friction between the implant and tissues during insertion, and prevents the accumulation of debris and bacteria in the pores. Further, the water soluble PA-PEG, PA-PEG blend, or PA-PEG/polymer blend is very slippery when wet and provides a lubricating layer that is continuously replaced as the implant is moved along tissue planes. After implantation, the pore-filling matrix dissolves and diffuses away, leaving an open porous structure for tissue ingrowth. Ideally, the properties of the PA-PEG or PAPEG/polymer matrix material will change from lubricious to adhesive as additional fluid is adsorbed, lessening the occurrence of malposition after initial implant placement. The PA-PEG or PA-PEG/polymer matrix used to fill the pores can additionally be formulated to contain pharmaceutical materials or drugs which are released slowly into the local region around the implant as the material dissolves or disperses. If prepared in an anhydrous formulation, the matrix allows for longer-term stability of some water-sensitive pharmaceutical compositions.

In a first preferred embodiment, a PA-PEG, PA-PEG blend, or PA-PEG/polymer blend, such as a blend of C50-PE PEG 16 and poloxamer 124, is applied to the surface of a porous implant, for example a coralline, porous hydroxyapatite implant, either at the time of manufacture of the implant or immediately before implantation. The solid PA-PEG material temporarily fills the spaces in the surface of the implant, making it smooth and slippery when in contact with tissue fluids, and easier to slide into position during surgery, but disappears from the pores after surgery, allowing tissue ingrowth into the open structure of the implant.

In a second preferred embodiment, a porous implant is manufactured so that its pores are largely or completely filled with a resorbable polymer. This can be achieved, for example, by placing a porous implant into molten PA-PEG, PA-PEG blend, or PA-PEG/polymer blend under a vacuum and allowing it to cool. The resulting implant can be cut or machined to shape, as needed, but retains a smooth, self-lubricating surface which allows it to glide along tissue planes, and prevents accumulation of debris within the pores. Porous polyethylene implants produced in this manner remain flexible because the PA-PEG, PA-PEG blend, or PA-PEG/polymer blend is relatively soft and malleable. Once implanted, vascular and soft tissue ingrowth into the pores of the implant will occur as the PA-PEG or PA-PEG blend is resorbed.

In a third preferred embodiment, a suitable PA-PEG, PA-PEG blend, or blend of a PA-PEG with another water-soluble or water-dispersible polymer is used for manufacturing a porous implant. The PA-PEG, PA-PEG blend, or PA-PEG/polymer blend is combined with fusible or bondable particles, such as polyethylene particles in the size range greater than about 35 microns to about 1.0 mm diameter, in an appropriate proportion to allow the majority of the particles to be in contact with one another. The combination is placed into a suitable mold, and a process that causes the particles to fuse together is applied to the combination. Such processes include a brief period of heating to above the melting point of the polyethylene particles, or initiation of a chemical reaction to create chemical bonds between the apposed surfaces of adjacent particles. The PA-PEG or PA-PEG blend may then be washed away from the porous implant using an appropriate solvent, such as acetone, or it may be left to act as a lubricant to ease the insertion of the implant during surgery.

Another preferred embodiment is an adhesive matrix for implantation formulated with an anhydrous PA-PEG, PA-PEG blend, or a PA-PEG/polymer blend and further containing one or more bioactive compounds. Many bioactive compounds are unstable and lose their biological activity in the presence of water. A primary issue, therefore, is to formulate a suitable matrix that contains no water, but which is also nontoxic, biocompatible, readily excreted, easy to use, and simple to manufacture. These advantages, its handling characteristics, and cohesive and adhesive properties, makes this matrix particularly well suited as an excipient and delivery system for bioactive substances. The anhydrous formulation has the benefit of protecting the activity of compounds that have limited stability in an aqueous environment, not only during manufacture and storage, but also after the material is implanted in the body. If a trace of water is present, the matirx can serve to bind the water to make it unavailable to interact with the drug. In addition, there is the benefit of being able to incorporate both hydrophilic and hydrophobic materials, which will be retained within the bulk of the excipient material and only released to the surrounding environment as the PA-PEG, PA-PEG blend, or PA-PEG/polymer blend dissolves. A further advantage is that when incorporated into the PA-PEG, PA-PEG blend, or PA-PEG/polymer blend, certain largely hydrophobic and poorly soluble molecules, drugs, or compounds, are readily dispersed into the body fluids by the PA-PEG as it dissolves. There is no prior art material known to have this combination of attributes.

A specific example of this preferred embodiment is an osteogenic paste comprising a PA-PEG blend or PA-PEG/polymer blend combined with one or more bioactive osteogenic compounds such as bone morphogenic protein (BMP), TGF-beta, or another agent that stimulates bone growth and optionally, inert particles such as hydroxyapatite or bioactive particles such a bone granules or DBM.

EXAMPLES

Example 1

Macroscopic Characterization of PE-PEG Blends

Two different PE-PEGs, C50 PE-PEG 16, and C33 PE-PEG 2.6, were obtained from Sigma-Aldrich (St. Louis, Mo.). These were combined with several different polyalkylene glycol polymers and copolymers, and evaluated as follows
Method 1:
Appropriate amounts of PE-PEG and the second polymer were placed into a sealed borosilicate glass container, and incubated in a laboratory oven at 125° C. for 24 hours. The samples were then mixed thoroughly while hot, poured into prewarmed nonstick metal molds, and rapidly cooled by placing the mold onto a cold plate maintained at minus 10° C. When removed from the mold, the PE-PEG/polymer blend was in the form of solid bars of approximate dimensions 2" by 0.6" by 0.125".
Method 2:
Borosilicate glass containers containing 10 g of PE-PEG and the second polymer in appropriate proportions heated in a laboratory microwave oven until as both components were observed to be fully melted (1 min to 2 min). The liquid polymer melt was mixed by shaking the hot containers, poured into open 10 ml polypropylene syringes and allowed to cool at room temperature for 24 hours. The syringe barrel was then cut though using a sharp blade and the solid polymer blend was pushed out as a rod using the syringe plunger. The material was then sliced into 0.75" diameter×0.125" discs prior to evaluation.
Evaluation of PE-PEG Blends:

After an initial mixing of the PE-PEG blends at 125° C., miscibility was determined in the molten state by rapidly inverting the sealed borosilicate glass containers and visual examination at 125° C. A clear single phase showed compatibility or true miscibility. Slight turbidity showed partial compatibility. The formation of droplets (akin to oil-in-water droplets), significant turbidity, or two distinct phases showed immiscibility.

As supplied, both PE-PEGs were hard and somewhat brittle waxes that could not be deformed by hand in the solid state. The polymers blended with the PE-PEGs were either liquids or soft pastes at 2500, with the exceptions of PEG 900 which was a soft solid and PEG 1450 which was solid. The difference in hardness of the two components in the solid phase allowed the compatibility of the PE-PEG and the second polymer to be rapidly screened by working a piece of each bar between gloved fingers. A granular texture and lack of cohesion after working indicated that phase separation had occurred before or during the cooling process. A smooth, homogeneous, wax-like consistency that maintained cohesion when kneaded suggested good compatibility. The most homogeneous blends, 050 PE-PEG 16 with poloxamer 124 or poloxamer 235 (PLURONIC™ L44 or P85, respectively) were studied in greater detail over a range of 10% to 90% w/w PE-PEG prepared using Method 2.
Results Shown in Table 2

Molten: RE-PEGs formed homogeneous mixtures with all but one of the poloxamers. They included poloxamers with a PEG content of greater than 10% w/w, and partial compatibility with low molecular mass PEG homopolymers and a poloxamer containing 10% PEG (PLURONIC™ L61). Combinations of PE-PEGs with poly(propylene glycol) and with a hydrophobic random EO/PO copolymer (EP530) formed a turbid liquid which separated into two distinct phases on standing. PE-PEGs formed very thick gel-like materials in the molten state with PEGs, the viscosity increased with increasing molecular mass of PEG.

Solid: Evaluation of solid bars confirmed the miscibility observations in the molten state, Miscible blends formed waxes that ranged from hard and brittle, to soft and grease-like with an even texture and no granularity. Blends containing 70% to 90% were generally soft waxy solids; those with a PE-PEG (w/w) content of 70% or lower were tacky or slippery grease-like substances. Immiscible combinations showed a characteristic granularity with hard particles of PE-PEG dispersed in the softer matrix of the second polymer. For those combinations in which the immiscible polymer was a liquid, the liquid polymer was expressed from the material as pressure was applied.

Results Shown in Table 3

The molten blends of C50 PE-PEG 16 with poloxamer 124 or poloxamer 235 were homogeneous clear liquids over the full range of blending proportions blends. After cooling, blends containing 100% to 20% poloxamer 124 or 20% to 40% poloxamer 235 (w/w) formed soft waxes that were easy to work between the fingers, but cohesive and adhesive to hard substrates. The properties of these blends appeared to be particularly good for bone hemostasis or a soft adhesive matrix for implanted particles. Blends containing a higher proportion of poloxamer to PE-PEG homogeneous ranged from tacky waxes to soft grease or jolly-like materials; these materials are considered to have particular utility as soluble or dispersible lubricants, matrix materials, excipients, and the like, for use in medicine, dentistry, and surgery.

TABLE 2

| Type of PE-PEG | Mixed with | Hot Melt | Phase separation | Evaluation | Impression |
|---|---|---|---|---|---|
| C33 PE-PEG 2.6 | PPG, MW 2000, 10%, 20%, 30% | Could be mixed, liquid | Yes | Brittle, crumbly, not cohesive, softer with more PPG | Poor cohesion, immiscible/ incompatible, not useful as wax |
| C50 PE-PEG 16 | | Harder to mix, slightly turbid liquid | Yes | Brittle, crumbly, not cohesive, softer and slippery with more PPG | Poor cohesion, immiscible/ incompatible, not useful as wax |
| C33 PE-PEG 2.6 | PPG, MW 4000 10%, 20%, 30% | Could be mixed, liquid | Yes | Brittle, crumbly, not very cohesive, softer and powdery with more PPG | Poor cohesion, immiscible/ incompatible, not useful as wax |
| C50 PE-PEG 16 | | Harder to mix, slightly turbid liquid | Yes | Brittle, crumbly, slippery, not cohesive, granular feel, softer with more PPG | Poor cohesion, immiscible/ incompatible, not useful as wax |
| C33 PE-PEG 2.6 | PT 7200 10%, 20%, 30% | Could be mixed, liquid | Yes | Hard to work initially, somewhat wax-like, but non homogeneous - fine grains suspended in an oil | Immiscible/ incompatible |
| C50 PE-PEG 16 | | Harder to mix, slightly turbid liquid | Yes | Brittle, slippery, nonhomogeneous, pasty/tacky at 30% | Immiscible/ incompatible |
| C33 PE-PEG 2.6 | EP530 10%, 20%, 30% | Could be mixed, liquid | Yes | Brittle, softer but crumbly with more added polymer | Immiscible/ incompatible |
| C50 PE-PEG 16 | | Harder to mix, slightly turbid liquid | Yes | Hard to work initially, soft and tacky at 30% | Partially compatible? |
| C33 PE-PEG 2.6 | PEG 900 10%, 20%, 30% | Turbid after mixing, liquid | Yes | Hard to work initially, softer, powdery feel and loss of cohesion with more PEG | Immiscible/ incompatible |
| C50 PE-PEG 16 | | Thick gel after mixing | No | Soft, wax-like, tacky at 20%, very tacky and liquid squeezes out at 30% | Partially compatible? May be a useful blend at <20% PEG |
| C33 PE-PEG 2.6 | PLURONIC L61 (poloxamer 181) 10%, 20%, 30% | Could be mixed, liquid | Yes | Hard to work initially, softer, powdery feel and loss of cohesion at 20%, 30% | Immiscible/ incompatible |
| C50 PE-PEG 16 | | Could be mixed, liquid | Yes | Wax-like, hard to start, softer but tacky at 20%, very tacky and crumbly at 30% | Partially compatible? May be a useful blend at <20% L61 |
| C33 PE-PEG 2.6 | PLURONIC P123 (poloxamer 403) 10%, 20%, 30% | Could be mixed, liquid | Yes | Hard to work initially, softer, powdery feel and loss of cohesion with 30% P123 | Immiscible/ incompatible |
| C50 PE-PEG 16 | | Could be mixed, liquid | Yes | Wax-like, hard to start, softer but tacky at 20%, very tacky and liquid squeezes out at 30% | Partially compatible? May be a useful blend at <20% P123 |
| C50 PE-PEG 16 | PEG 400 10%, 20%, 30% | Viscous, gel-like, slightly turbid | No | 10% hard to start, 20% soft, 30% very soft, all remain as cohesive soft waxes with working. | All good waxes, soft (10%) to very soft (30%) - slightly oily, appear to be compatible but not fully miscible |
| C50 PE-PEG 16 | PEG 600 10%, 20%, 30% | Very viscous, gel-like | Slight? | Hard to start, softens quickly 20%, 30% very soft/tacky, lumps. | OK waxes, soften with working, but become tacky - not fully miscible |
| C50 PE-PEG 16 | PEG 1450 10%, 20%, 30% | Viscous, gel-like | Yes | Very hard to start, 10% brittle, 30% becomes oily wax with work, but may not be not fully cohesive | Harder waxes which become oily with working - incompletely miscible |
| C50 PE-PEG 16 | PLURONIC L44 (poloxamer 124) 10%, 20%, 30% | Free-flowing clear liquid | No | 10% hard to start, 20% soft, 30% very soft, all remain as cohesive soft waxes with working | All good waxes, hard (10%) to very soft (30%) - seems like a fully miscible blend |

TABLE 2-continued

| Type of PE-PEG | Mixed with | Hot Melt | Phase separation | Evaluation | Impression |
|---|---|---|---|---|---|
| C50 PE-PEG 16 | PLURONIC P85 (poloxamer 235) 10%, 20%, 30%, 40% | Free-flowing clear liquid | No | All hard to work initially, need significant effort. 20%, 30% blends are good waxes, 40% is softer and slippery | Miscible blend, makes good waxes, softness controlled by proportion of P85 |

TABLE 3

| C50 PE-PEG 16 (%) | Poloxamer 124 (%) | Appearance (solid) | Properties |
|---|---|---|---|
| 10 | 90 | White stick | Grease |
| 20 | 80 | White shiny stick | Oily cream/grease |
| 30 | 70 | White stick | Oily, tacky cream, adhesion > cohesion (unable to keep in a ball) |
| 40 | 60 | White stick | Tacky, oily, cohesion just adequate to keep together |
| 50 | 50 | White stick | Tacky, oily, adhesive, cohesive |
| 60 | 40 | Off-white stick | Very soft, oily, very tacky after working, cohesion > adhesion |
| 70 | 30 | Cream stick | Very soft, oily, becomes tacky with working |
| 80 | 20 | Cream stick | Softer than 90/10 -cuts like butter, easy to work, tacky with working |
| 90 | 10 | Cream stick | Soft, easy to work. |

| C50 PE-PEG 16 (%) | Poloxamer 235 (%) | Appearance (solid) | Properties |
|---|---|---|---|
| 10 | 90 | Off-white stick | Oily grease |
| 20 | 80 | Off-white stick | Oily cream/grease |
| 30 | 70 | Off-white stick | very tacky paste - unable to keep sample in a ball |
| 40 | 60 | Off-white stick | Tacky paste - able to keep in a ball (just) |
| 50 | 50 | Off-white stick | Very soft, oily feel - becomes tacky with a little working |
| 80 | 40 | Off-white stick | Soft, easy to work, tacky after a little working |
| 70 | 30 | Cream stick | Soft, easy to work, a little tacky with a lot of working |
| 80 | 20 | Cream stick | Softer than 90/10 - cracks when folded, soft wax with working |
| 90 | 10 | Cream stick | Hard, snaps when folded, after working does not stay together |

Example 2

Microscopic Evaluation of PE-PEG/Poloxamer Binary Blends

A poloxamer-PE-PEG combination that blended well and formed a smooth homogeneous single phase both in the molten and solid state was examined for evidence of any phase separation on the microscopic scale.

Method: C50 PE-PEG16 (Sigma-Aldrich) was blended with poloxamer 124 (P124) as described in Example 1 in proportions ranging from 10% P124 to 90% P124. While molten, approximately 20 microliters of each blend was placed onto a glass microscope slide preheated to approximately 150° C. and covered with a glass cover slide. The slide was then placed on a microscope equipped with Nomarski differential interference contrast optics, and observed at 400× magnification as the polymer blend cooled to room temperature.

Results: While liquid, blends of the two polymers were macroscopically water-clear with no turbidity, Schlieren effect, or other evidence of phase separation. Microscopically, it was apparent that the liquid blend was a single phase, with the exception of a few small spherical bubbles of an immiscible liquid component present at much less than 0.1%.

There was no evidence of phase separation as the liquid blend cooled and solidified. The PE-PEG component crystallized from a large number of independent foci in each optical field, with the leading fronts of the crystallization spreading throughout the liquid until encountering each other, leaving clearly-defined crystal domains. As shown in FIG. 1, for blends of all proportions from 10% P124 to 90% P124, the PE-PEG crystal structure filled the entire field, with no gaps or spaces or any other evidence that the distribution of P124 was nonhomogeneously distributed thought the solid blend. Visually, the appearance of all blends from 10% P124 (90% PE-PEG) to 70% P124 (30% PE-PEG) was essentially similar; for the 90% P124 (10% PE-PEG) blend, the crystal structure was more open, with longer individual crystals. These results were consistent with the bulk properties of the blends, which were waxy solids at room temperature over the range 10% P124 to 50% P124, becoming increasingly softer with an increase the P124 content. Blends with 70% and 90% P124 were a soft wax and a very soft wax/grease, respectively.

Conclusion: The binary system of poloxamer 124 and C50 PE-PEG16 formed stable blends with no evidence of phase separation in either the molten or solid state over a wide range of proportions. The miscibility of the polymers causes the blend to behave as an alloy physical properties that depend upon the relative proportions of the two component polymers, and exhibit advantageous properties that are not exhibited by either component polymer alone. The discovery of novel blends of PE-PEG with other biocompatible, water-soluble polymers is an unexpected result, because most binary combinations of different polymers, even polymers that are chemically closely related, are usually incompatible and immiscible, and spontaneously separate into individual phases.

As shown in Tables 2 and 3, blends of poloxamer 235 (PLURBNIC™ P85, BASF) with C50 PE-PEG16 also formed homogeneous and stable solids over a range of concentrations, indicating that this combination also forms a miscible blend. Certain other poloxamers, and other related block copolymers, may also be compatible with PE-PEGs and PA-PEGs of other types. In particular, advantageous compositions can be made by blending PA-PEGs with other poloxamers such as L186 and P303 (also known as PLURONIC™ L64 and P103, BASF) that are liquid or pastes in the temperature range from 4° C. to 40° C.

Example 3

Waxy PE-PEG Composition for Bone Hemostasis

A preferred waxy material with utility as a bone hemostasis agent may be produced in the following manner. Approximately 900 of C50 PE-PEG 16 and 100 g of poloxamer P124, preferably PLURONIC™ L44NF (BASF), are placed into a sealed PYREX® glass container and heated to a temperature of 110° C. in an oven. The flask is placed on a roller mixer until the contents are fully blended together to form a low-viscosity light yellow liquid, and then allowed to rest at 110° C. until all air bubbles have escaped from the liquid. The liquid is then dispensed directly into TEFLON® coated metal molds maintained at a temperature of 110° C. The molds are covered and allowed to cool to room temperature for up to 24 hours. The solid PE-PEG/polymer blend is removed and placed into individual foil packets lined with a polyethylene coating. These packets are then placed into pouches suitable for sterile implantable devices, and the hemostatic material is sterilized using an electron beam or gamma irradiation.

Example 4

Bone Filler Composition

A preferred putty-like composition with utility as a bone filler may be produced in the following manner: A ratio of three parts by weight of C50 PE-PEG 16 and one part by weight of 100 g of poloxamer P124, preferably PLURONIC™ L44NF (BASF), are placed into a sealed PYREX® glass container and heated to a temperature of 110° C. in an oven. The flask is placed on a roller mixer until the contents are fully blended together to form a low-Viscosity light yellow liquid, and then allowed to rest at 110° C. until all air bubbles have escaped from the liquid. The liquid is then pored into an appropriate wide-necked container, and allowed to cool to room temperature, forming a soft waxy solid.

Two parts by volume of the soft PE-PEG/polymer blend and three parts by volume of polyethylene particles ranging in size from 50 microns to 300 microns are mechanically kneaded together at room temperature or below until the particles are fully and homogeneously incorporated into the PE-PEG/polymer blend. If desired, the mixture may then be maintained under vacuum for 24 hours to allow air bubbles to escape from within the formulation. The formulation is then dispensed directly into plastic syringes of volumes from 1-5 cc, which have been modified to eliminate the usual luer tip, and instead have a wider opening of at least 3-4 mm diameter opposite the plunger. The open ends of the filled syringes are then capped, and the syringes placed into individual foil packets lined with a polyethylene coating. The product is sterilized using the appropriate dose of plasma radiation. Other preferred compositions may be produced in a very similar manner using other particles such as hydroxylapatite granules, bone chips, or DBM. The consistency of any of these compositions can be varied from a soft paste to a hard putty in at least four ways: by combining the PE-PEG and polymer in different proportions; by selecting a different PE-PEG or polymer; by incorporating a higher or lower volume fraction of particles into the formulation, or by selecting particles of a different size and shape.

Example 5

Hemolysis and Cytotoxicity

Materials to be used for implantation in the body must be biocompatible and nontoxic to cells, especially the cells of the tissue in immediate contact with the implant. Two standard tests are performed to evaluate cellular toxicity and biocompatibility. The hemolysis test detects whether the red blood cell menbrane is damaged by exposure to the substance. The cytotoxicity test examines longer term biocompatibility with living cells in culture.

Figure 1A:
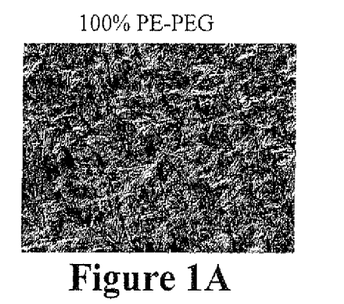
FIG. 1 shows microscopic images of blends of C50 PE-PEG16 with poloxamer 124. No evidence of separate phases was observed for blending proportions from 9:1 to 1:9.
Figure 1B:
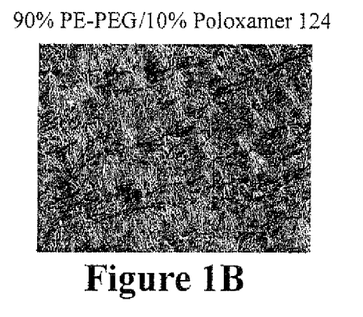
Figure 1C:
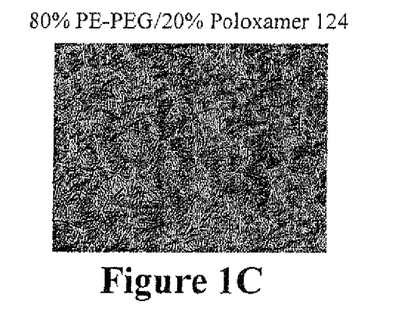
Figure 1D:
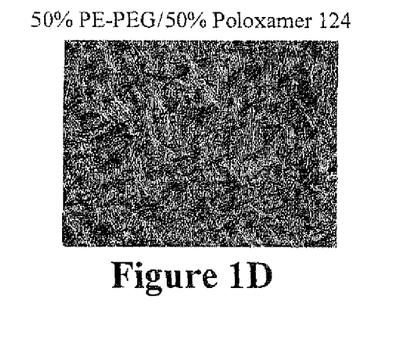
Figure 1E:
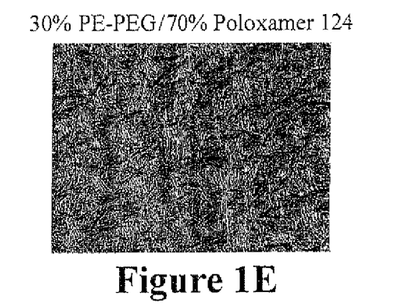
Figure 1F:
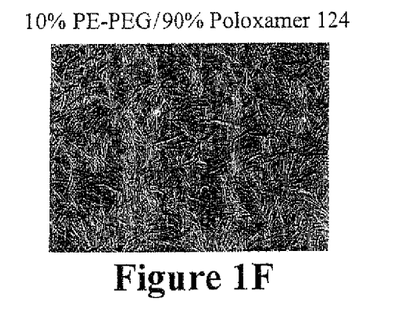
Figure 1G:
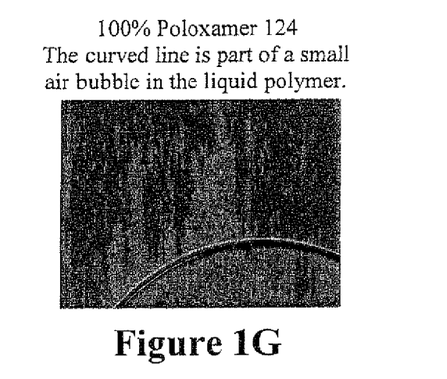
Figure 2:
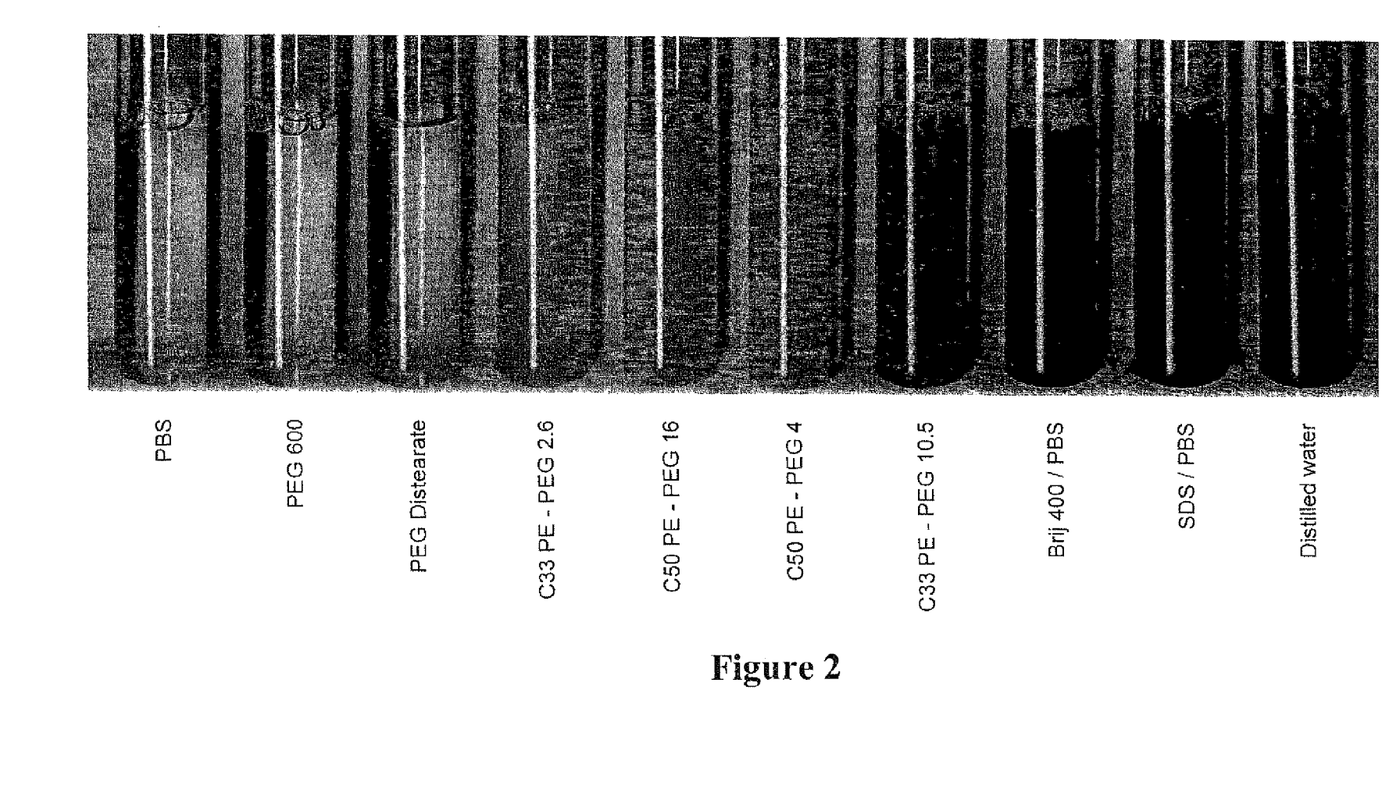
FIG. 2 shows the hemolytic effects of PE-PEG material and other reference compounds on human red blood cells (RBCs). For all tubes, intact RBCs have been removed by centrifugation. The tubes with a colored solution contain hemoglobin released from the RBCs, indicating hemolysis.

Hemolysis: Polypropylene 15 ml test tubes were filled to the 10 ml mark with isotonic buffered solutions of PE-PEGs and other reference compounds as positive and negative controls, as follows (from right to left in FIG. 2):

1) PBS alone, the negative control
2) PEG 600
3) PEG 400 distearate, a linear PEG molecule conjugated to two C18 alkane chains, one at each end of the PEG
4) C33 PE-PEG 2.6, a PE-PEG with short PEG segments
5) C50 PE-PEG 16
6) C50 PE-PEG 4, a higher molecular weight PE-PEG with a ratio of PE to PEG similar to #4
7) C33 PE-PEG 10.5, similar to #4 but with longer PEG segments
8) Brij 700) a nonionic surfactant fatty ether produced from stearyl alcohol and ethylene oxide, equivalent to C18 PE-PEG 100
9) Sodium dodecyl sulfate, a sulfated alkane ionic detergent
10) Distilled water which causes osmotic lysis of the RBCs (i.e., the positive control)

Two milliliters of a 40% v/v suspension of washed red blood cells (RBCs) was added to each tube, and incubated with the test solution 37° C. for two hours. The tubes were then centrifuged at 1750 g for 10 minutes to sediment the intact RSCs. Hemoglobin in the supernatant above the packed RBCs indicates hemolysis.

Results: The presence of absence of significant hemolysis is clearly visible in tubes 7 to 10 in FIG. 2. Tubes 8 and 9 contained strong surfactants which are known to disrupt the lipid bilayer of the RBC membrane. C33 PE-PEG 10.5 (tube 7) also caused significant hemolysis, but no evidence of hemolysis was observed with the other PE-PEGs, including PEG distearate or PEG alone.

Conclusion: Higher molecular weight PE-PEGs, such as the C50 compounds, do not cause hemolysis. Some PE-PEGs with shorter alkane chains (e.g., C33 PE-PEG 10.5 and Brij 700) did cause hemolysis but others did not. It is likely that the hemolytic potential depends upon both the absolute molecular weight of the PE and PEG blocks and also the relative hydrophilic-lipophilic balance (HLB) of the molecule, such each hydrated PEG block multiplied by number of PEG blocks present. Table 4 shows the results of such calculations for PE-PEGs, compared to other hydrophilic polymers.

TABLE 4

|  | C50/ E16 | C50/ E4 | C33/ E10.5 | C33/ E2.6 | Poloxamer 188 | PEG 6000 |
|---|---|---|---|---|---|---|
| Moles of EO per PEG block | 16 | 4 | 10.5 | 2.6 | 150 | 136 |
| PEG block intrinsic viscosity ($\eta$) ml/g | 3.93 | 1.56 | 2.99 | 1.17 | 18.2 | 17.2 |
| Proportion of PEG in molecule (w/w) | 0.5 | 0.2 | 0.5 | 0.2 | 0.8 | 1.0 |
| Maximum swelled volume (Vs) per g | 2.52 | 1.19 | 2.05 | 1.11 | 13.4 | 15.6 |
| Vs when 10% of material hydrated | 1.15 | 1.02 | 1.10 | 1.01 | 2.24 | 2.46 |
| Relative to PEG 6000 (%) | 10.4% | 1.3% | 7.2% | 0.8% | 84.9% | 100% | that compounds with a very small PEG component are very weak surfactants and unable to disrupt the integrity of the RBC membrane lipids.

Cytotoxicity C50 PE-PEG 16 was evaluated for cytotoxicity by an agar diffusion test as defined by ISO 10993-5 (1999). Samples of the PE-PEG were molded into thin discs, and laid over a cell culture of mouse fibroblasts (L929 cells) in soft agar; an equivalent piece of natural rubber was used as a positive control. The reaction of the cells to the specimen was evaluated under the microscope after 24 hours and 48 hours of culture at 37° C., and graded on a scale of 0 to 5, corresponding to no detectable effect (grade 0) to a severe effect that extends to a zone 1 cm beyond the area exposed to the specimen (grade 4).

Results: C50 PE-PEG 16 showed a grade 1 reaction at 24 hours, and grade 2 at 48 hours, corresponding to a mild effect on the cells directly under the specimen. The positive control showed grade 3 response with a zone of influence extending for 7 mm beyond the area or exposure.

Conclusion: Mild biological activity grade 2 is considered to be a negative result, indicating that C50 PE-PEG 16 is noncytotoxic.

Example 6

Calculation of Maximal Swelling Potential

Solid hydrophilic polymers will show some initial increase in overall volume after exposure to water, which will depend upon the relative rates at which water is absorbed into the bulk of the material and the rate at which the material fully dissolves and migrates away from the surface. A desired material for implantation does not significantly swell after exposure to body fluids, does not dissolve immediately, and will remain at the site for a few hours to several so days. It is difficult to model the swelling potential of a solid polymer in vitro, since many assumptions must be made about the rate of movement of dissolved material away from the bulk phase, which depends not only on how fast the material can dissolve, but also on the viscosity of the solution and the restriction to flow presented by the surrounding tissues.

It is possible, however, to calculate a theoretical upper limit of swelling for a hydrophilic polymer if the intrinsic viscosity of the polymer is known. The intrinsic viscosity is a measure of the volume occupied by the fully-hydrated polymer at infinite dilution, at which point each polymer molecule is separated from any other. Since the PE component of the PE-PEG molecule can be considered to be completely hydrophobic, then the maximum volume of the hydrated PE-PEG molecule will be equal to or less than that of a PEG molecule of the same molecular weight, and the total volume occupied of the PE-PEG when fully dissolved is given by the volume to The intrinsic viscosity for a PEG molecule equivalent to the PEG block is calculated from the PEG molecular weight using the Mark-Houwink equation. The maximum swelling per gram of material is calculated as the volume occupied by an equivalent PEG molecule multiple by the mass fraction of PEG in the molecule. It can be seen that the hydrated volume (Vs) occupied by poloxamer 188, which contains about 80% PEG by mass, and pure PEG 6000 would be 13-15 times higher than the volume of the solid material. In contrast, the maximum increase in volume predicted for the PE-PEGs is about 150% (2.52 per g for C50 PE-PEG16) and lower. Everything else being equal, the maximum swelling of C50 PE-PEG16 would be predicted to be about 10% that of PEG 6000.

In practice, only a small proportion of the polymer would be hydrated at any time, before dissolving fully and diffusing away from the site. Assuming 10% average hydration at any time (i.e., 10% of the polymer is fully hydrated, or all polymer is 10% hydrated, or somewhere in between) then the maximal possible swelling for C50 PE-PEG16 would be 15%, compared to about 150% for PEG 6000.

It can be seen that PE-PEGS have a considerably lower maximal swelling potential than other types of biocompatible polymer that are commonly used in hydrogel formulations. This theoretical limit would never be approached in practice, and many other factors will modify the actual swelling, as previously discussed, but it is useful as a means to compare the underlying swelling behavior different polymers.

Example 7

Incorporation of Hydrophobic and Hydrophilic Dyes in a PE-PEG/Polymer Blend Matrix The objective of these studies was to determine whether strongly hydrophobic and hydrophilic compounds can be readily incorporated into an anhydrous PE-PEG or PE-PEG/polymer blend, and to model their retention and release of such compounds from the PE-PEG material when it is placed in an aqueous environment.

Solvent Red 24 (SR24, CI 26105, also known as Sudan IV) was chosen as the hydrophobic test substance. SR24 is a very hydrophobic and lipophilic red dye used to label hydrocarbon fuels such as kerosene, to color waxes, and as a selective histological stain for fats and oils. SR24 is very soluble in hydrocarbon solvents, but has negligible solubility in water.

Rose Bengal (CI 45440, acid red 94) a rose-pink dye with a high solubility in water (36% w/w) was selected as the model hydrophilic agent. Rose Bengal is commonly used in medicine as a marker dye, such as to viualize damage to the conjunctiva of the eye.

Method: C50 PE-PEG16 was blended with PLURONIC™ L44 in a ratio of 7:3 w/w as described in Example 3. Rose Bengal (100 mg) and SR24 (100 mg) were mixed with 5 g aliquots of molten PE-PEG and PE-PEG/poloxamer blend, and maintained at 110° C. with mixing until the dye was fully dissolved.

Ten small (6 ml) glass test tubes were prepared as shown in Tables 5-6, Tubes 4-7 contained 0.5 g of the PE-PEG and PE-PEG/polymer samples mixed with dye, tubes 2, 3, 8 and 9 contained 0.5 g PE-PEG and PE-PEG/polymer samples (without dye) and 10 mg of dye added separately (after the PE-PEG or blend had solidified), tubes 1 and 10 contained only the dye, as controls.

TABLE 5

Hydrophilic Dye (Rose Bengal)

| Tube | Contents | Max. Conc. (µg/ml) | Time to max. conc. |
|---|---|---|---|
| 1 | Dye only | 210 | immediate |
| 2 | PE-PEG, dye, unmixed | 211 | immediate |
| 3 | PE-PEG/polymer blend, dye, unmixed | 213 | Immediate |
| 4 | Dye dispersed in PE-PEG | 5 | >6 days |
| 5 | Dye dispersed in PE-PEG/polymer blend | 47 | ≈6 days |

TABLE 6

Hydrophobic Dye (SR24, Solvent Red 24)

| Tube | Contents | Max. Conc. (µg/ml) | Time to max. conc. |
|---|---|---|---|
| 6 | Dye dispersed in PE-PEG/polymer blend | 4.6 | >6 days |
| 7 | Dye dispersed in PE-PEG | 12.3 | ≈3 days |
| 8 | PE-PEG/polymer blend, dye, unmixed | 0.7 | — |
| 9 | PE-PEG, dye, unmixed | 6.8 | >6 days |
| 10 | Dye only | 0.0 | — |

Each glass test tube was affixed to the inside of a 50 ml polypropylene centrifuge tube with a silicone adhesive. Fifty ml of phosphate buffered saline was added to each of the tubes, and they were rocked gently for six days. At appropriate time points, the concentration of dye in the buffer was measured using a spectrophotometer. The SR24 dye was measured at 516 nm, the Rose Bengal concentration was estimated from the maximal absorption $\lambda_{max}$ from 540 nm to 560 nm.

Results: Both dyes readily melted and/or dissolved in the PE-PEG and PE-PEG/poloxamer blend at 110° C., forming an optically clear red or pink solution with no trace of undissolved dye. When cooled, the solid waxes were uniformly dark red and dark pink, with no evidence of inhomogeneity in the distribution of either dye.

Rose Bengal dye dissolved immediately upon contact with water (tubes 1 to 3), but the dye contained within the PE-PEG or PE-PEG blend (tubes 4 and 5) dissolved more slowly, especially for the PE-PEG alone (tube 5) indicating that the dye is shielded from contact with the water. The more hydrophilic PLURONIC™ L44 component in tube 4 apparently increased the hydration fate compared to tube 5, and hastened release of dye.

The hydrophobic SR24 dye showed zero solubility in water (tube 10), and the presence of the PE-PEG/PLURONIC™ L44 blend (tube 8) did not result in significant solubilization of the dye. The aqueous solubility of SR24 was apparently greatly enhanced after incorporation into the PE-PEG (tube 7) and the red dye was evenly dispersed or dissolved throughout the buffer, reaching an equilibrium concentration after three days. The presence of PLURONIC™ L44 in the blend (tube 6) reduced or slowed the transfer of SR24 to the aqueous phase, the opposite of the effect observed with Rose Bengal. An unexpected observation was that the PE-PEG without PLURONIC™ L44 (tube 9) also facilitated the transfer of SR24 to the aqueous phase. Poloxamers and PE-PEGs both have surfactant properties, so it was anticipated that some degree of enhanced solubility of the hydrophobic dye might be observed in these studies, but the finding that the PE-PEG was considerably more effective than the poloxamers was unexpected.

In conclusion PE-PEG, either on its own or blended with another component, has the ability to dissolve both hydrophobic and hydrophilic molecules in the absence of water, and surprisingly, to both facilitate the release of a very hydrophobic model compound into an aqueous medium in which it is usually insoluble, and to control the rate of release of a very hydrophilic compound that would otherwise dissolve almost immediately. For solubilizing a hydrophobic compound, PE-PEG was superior to a poloxamer surfactant. This combination of properties, together with the desirable handling characteristics of the material (i.e., malleable, flexible, adhesive, and cohesive), is unexpected and previously unknown in a single class of biocompatible material, and clearly advantageous for many diverse medical, dental, and surgical uses.

All patents, patent applications, and other publications cited herein are incorporated by reference in their entirety.

All modifications and substitutions that come within the meaning of the claims and the range of their legal equivalents are to be embraced within their scope. A claim using the transitional term "comprising" allows the inclusion of other elements to be within the scope of the claim; the invention is also claimed by using the transitional phrase "consisting essentially of" (i.e., allowing the inclusion of other elements to be within the scope of the claim if they do not materially affect operation of the invention) or the transitional term "consisting" (i.e., allowing only the elements listed in the claim other than impurities or inconsequential activities which are ordinarily associated with the invention) instead of the "comprising" term. Any of the three transitions can be used to claim the invention.

It should be understood that an element described in this specification should not be construed as a limitation of the claimed invention unless it is explicitly recited in the claims. Thus, the claims are the basis for determining the scope of legal protection granted instead of a limitation from the specification which is read into the claims, In contradistinction, the prior art is explicitly excluded from the invention to the extent of specific embodiments that would anticipate the claimed invention or destroy novelty.

Moreover, no particular relationship between or among limitations of a claim is intended unless such relationship is explicitly recited in the claim (e.g., the arrangement of components in a product claim or the order of steps in a method claim is not a limitation of the claim unless explicitly stated to be so). All possible combinations and permutations of the individual elements disclosed herein are considered to be aspects of the invention; similarly, generalizations of the invention's description are considered to be part of the invention.

From the foregoing, it would be apparent to a person of skill in this art that the invention can be embodied in other specific forms without departing from its spirit or essential characteristics. The described embodiments should be considered only as illustrative, not restrictive, because the scope of the legal protection provided for the invention will be indicated by the appended claims rather than by this specification.

We claim:

1. A flowable or malleable polymer composition in an essentially dry form, comprising:
   (a) a poly(alkylene)-poly(ethylene glycol) block copolymer and
   (b) a poly(alkylene glycol) polymer or copolymer, which is prepared by blending together components (a) and (b) without the addition of water or other liquid.

2. The composition of claim 1, wherein the poly(alkylene glycol) polymer or copolymer is a poly(propylene glycol)-poly(ethylene glycol) copolymer.

3. The composition of claim 2, wherein the poly(propylene glycol)-poly(ethylene glycol) copolymer is a triblock copolymer having a poly(propylene glycol) block with a molecular mass in the range 300 and 10,000 g/mol, and two poly(ethylene glycol) blocks with a combined molecular mass in the range 300 to 10,000 g/mol.

4. The composition of claim 1, wherein components (a) and (b) are biocompatible and substantially nontoxic.

5. The composition of claim 1, wherein components (a) and (b) form a miscible blend.

6. The composition of claim 1, wherein the poly(alkylene)-poly(ethylene glycol) block copolymer is a diblock copolymer comprised of a poly(alkylene) block containing from 40 to 500 carbon atoms and a poly(ethylene glycol) block containing from 3 to 300 ethylene glycol units, the copolymer as a whole having a molecular mass in the range of about 700 g/mol to about 20,000 g/mol.

7. The composition of claim 6, wherein the poly(alkylene) block of the poly(alkylene)-poly(ethylene glycol) copolymer is a poly(ethylene) block with a molecular mass in the range from about 500 to about 7,000 g/mol.

8. The composition of claim 7, wherein the poly(alkylene glycol) polymer or copolymer is a poly(propylene glycol)-poly(ethylene glycol) copolymer.

9. The composition of claim 8, wherein the poly(propylene glycol)-poly(ethylene glycol) copolymer is a triblock copolymer having a poly(propylene glycol) block with a molecular mass in the range 300 and 10,000 g/mol, and two poly(ethylene glycol) blocks with a combined molecular mass in the range 300 to 10,000 g/mol.

10. The composition according to claim 1, wherein said composition can adhere to bone, tooth, skin, mucous membranes or other body tissues.

11. A composition for use in medicine, dentistry, or surgery comprised of:
    (a) at least one bioactive agent, medical/surgical device, or other therapeutic product and
    (b) the polymer composition of claim 1.

12. A method for medical, dental, or surgical treatment of a subject comprising:
    (a) providing the polymer composition of claim 1 and
    (b) administering said polymer composition to the subject as an adhesive, cohesive, filler, lubricant, or any combination thereof.

13. A composition for use in medicine, dentistry or surgery comprised of:
    (a) at least one bioactive agent, medical/surgical device, or other therapeutic product and
    (b) the polymer composition of claim 2.

14. A method for medical, dental or surgical treatment of a subject comprising:
    (a) providing the polymer composition of claim 2 and
    (b) administering said polymer composition to the subject as an adhesive, cohesive, filler, lubricant, or any combination thereof.

15. A composition for use in medicine, dentistry or surgery comprised of:
    (a) at least one bioactive agent, medical/surgical device, or other therapeutic product and
    (b) the polymer composition of claim 8.

16. A method for medical, dental or surgical treatment of a subject comprising:
    (a) providing the polymer composition of claim 8 and
    (b) administering said polymer composition to the subject as an adhesive, cohesive, filler, lubricant, or any combination thereof.

17. A composition for use in medicine, dentistry or surgery comprising:
    (a) biocompatible, inert particles and
    (b) the polymer composition of claim 1, wherein said particles are bound together by said polymer composition.

18. The composition of claim 17, wherein said particles are selected from the group consisting of bone chips or powder, demineralized bone, hydroxyapatite, polyethylene, and any combination thereof.

19. The composition of claim 18, wherein said particles occupy from 10% by volume to 64% by volume of said composition.

20. The composition of claim 17, wherein said particles have a size from 35 microns to 500 microns.

21. A composition for use in medicine, dentistry or surgery comprising:
    (a) biocompatible, inert particles and
    (b) the polymer composition of claim 2, wherein said particles are bound together by said polymer composition.

22. The composition of claim 21, wherein said particles are selected from the group consisting of bone chips or powder, demineralized bone, hydroxyapatite, polyethylene, and any combination thereof.

23. The composition of claim 22, wherein said particles occupy from 10% by volume to 64% by volume of said composition.

24. The composition of claim 21, wherein said particles have a size from 35 microns to 500 microns.

25. A composition for use in medicine, dentistry or surgery comprising:
(a) biocompatible, inert particles and
(b) the polymer composition of claim 8, wherein said particles are bound together by said polymer composition.

26. The composition of claim 25, wherein said particles are selected from the group consisting of bone chips or powder, demineralized bone, hydroxyapatite, polyethylene, and any combination thereof.

27. The composition of claim 26, wherein said particles occupy from 10% by volume to 64% by volume of said composition.

28. The composition of claim 25, wherein said particles have a size from 35 microns to 500 microns.

29. A composition for use in medicine, dentistry or surgery comprised of:
(a) at least one bioactive agent, medical/surgical device, or other therapeutic product and
(b) a flowable or malleable polymer composition comprising two or more poly(alkylene)-poly(ethylene glycol) block copolymers having different melting points, such that at least one copolymer is a solid at about 37° C. and at least one other copolymer is a paste or liquid at about 37° C.

30. A method for medical, dental or surgical treatment of a subject comprising:
(a) providing a flowable or malleable polymer composition comprising two or more poly(alkylene)-poly(ethylene glycol) block copolymers having different melting points, such that at least one copolymer is a solid at about 37° C. and at least one other copolymer is a paste or liquid at about 37° C. and
(b) administering said polymer composition to the subject as an adhesive, cohesive, filler, lubricant, or any combination thereof.

* * * * *

UNITED STATES PATENT AND TRADEMARK OFFICE
CERTIFICATE OF CORRECTION

PATENT NO.         : 8,455,000 B2                                              Page 1 of 1
APPLICATION NO.    : 12/302288
DATED              : June 4, 2013
INVENTOR(S)        : Fisher et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 870 days.

Signed and Sealed this
Eighth Day of September, 2015

Michelle K. Lee
*Director of the United States Patent and Trademark Office*